United States Patent [19]

Iosif

[11] Patent Number: 4,619,273

[45] Date of Patent: Oct. 28, 1986

[54] DEVICE FOR DIAGNOSING AND MONITORING UROLOGICAL DISEASES

[76] Inventor: Baumberg Iosif, 54 Bay 29 St. #B5, Brooklyn, N.Y. 11214

[21] Appl. No.: 520,348

[22] Filed: Aug. 4, 1983

[51] Int. Cl.$^4$ .............................................. A61B 5/00
[52] U.S. Cl. .................................. 128/771; 137/123; 137/136
[58] Field of Search ........................ 128/771, 760, 762; 137/123, 130, 132, 136, 138; 73/861, 861.39, 861.41, 195

[56] References Cited

U.S. PATENT DOCUMENTS

| | | | |
|---|---|---|---|
| 373,885 | 11/1887 | Cunte | 137/136 |
| 2,525,342 | 10/1950 | Frie | 137/123 |
| 3,797,513 | 3/1974 | Hazen | 137/132 |
| 4,157,717 | 6/1979 | Goldberg | 604/32 |
| 4,187,722 | 2/1980 | Layton | 128/771 |
| 4,200,112 | 4/1980 | McWhorter | 128/771 |
| 4,343,316 | 8/1982 | Jespersen | 128/771 |
| 4,417,585 | 11/1983 | Frank | 128/771 |

FOREIGN PATENT DOCUMENTS 0038783 10/1981 European Pat. Off. ............ 128/771

Primary Examiner—Edward M. Coven

[57] ABSTRACT

A device for diagnosing and monitoring urological diseases includes a determining unit for determining at least one characteristic of patient's urination such as a urine exit speed variation or a urine quantity variation over a period of time. Both characteristics can also be determined simultaneously by the unit. A urine receiving element for a patient and a characteristic recording element for a physician can be formed as separate units located remotely from one another.

10 Claims, 4 Drawing Figures

DEVICE FOR DIAGNOSING AND MONITORING UROLOGICAL DISEASES

BACKGROUND OF THE INVENTION

The present invention relates to a device for diagnosing and monitoring urological diseases.

It is known that urological diseases, such as for example prostate, phimosis and the like affect the process of urination. The urological diseases are diagnosed in general by palpation and analysis of patient's complaints. It is to be understood that such a method is uncomfortable for patients, subjective and inaccurate. Monitoring of urological diseases is performed by complicated laboratory methods, including X-rays and others, and also observation of patient's urination. These methods also possess some disadvantages. It is therefore advisable to develop accurate and convenient devices for diagnosing and monitoring urological diseases.

SUMMARY OF THE INVENTION

Accordingly, it is an object of the present invention to provide a device for diagnosing and monitoring urological diseases, which avoids the disadvantages of the prior art.

More particularly, it is an object of the present invention to provide a device which can be used for diagnosing of urological diseases, determines quantitative and qualitative dynamics of variations of patient's urinations corresponding to the type and stage of the respective disease, helps a physician to monitor the results of treatment and dynamics of progressing of the diseases.

It is also an object of the present invention to provide a device which makes possible conducting of mass urological examinations.

In keeping with these objects and with others which will become apparent hereinafter, one feature of the present invention resides, briefly stated, in a device for diagnosing and monitoring urological diseases, which has means for determining variations of at least one parameter of urinations of a patient over a period of time.

Means for determining can include means for determining variations of an exit speed of a urine stream during urination of a patient over a period of time and/or means for determining variations of a quantity of urine flowing out during urination of a patient over a period of time, as a function of time.

The determining means can includes sensing means onto which patient's urine directly acts, for example at a location remote from a physician's room, and indicating means which receives signals from the sensing means and displays the respective data in the physician's room. This makes the use of the device more comfortable and less embarassing for a patient.

The deternining means which determine the above mentioned parameters provide accurate and sufficient data about the beginning and progress of urological diseases, results of their treatment etc.

The novel features of the present invention are set forth in the appended claims. The invention itself, however, will be best understood from the following description of a preferred embodiment which is accompanied by the following drawings.

DESCRIPTION OF A PREFERRED EMBODIMENT

Figure 1:
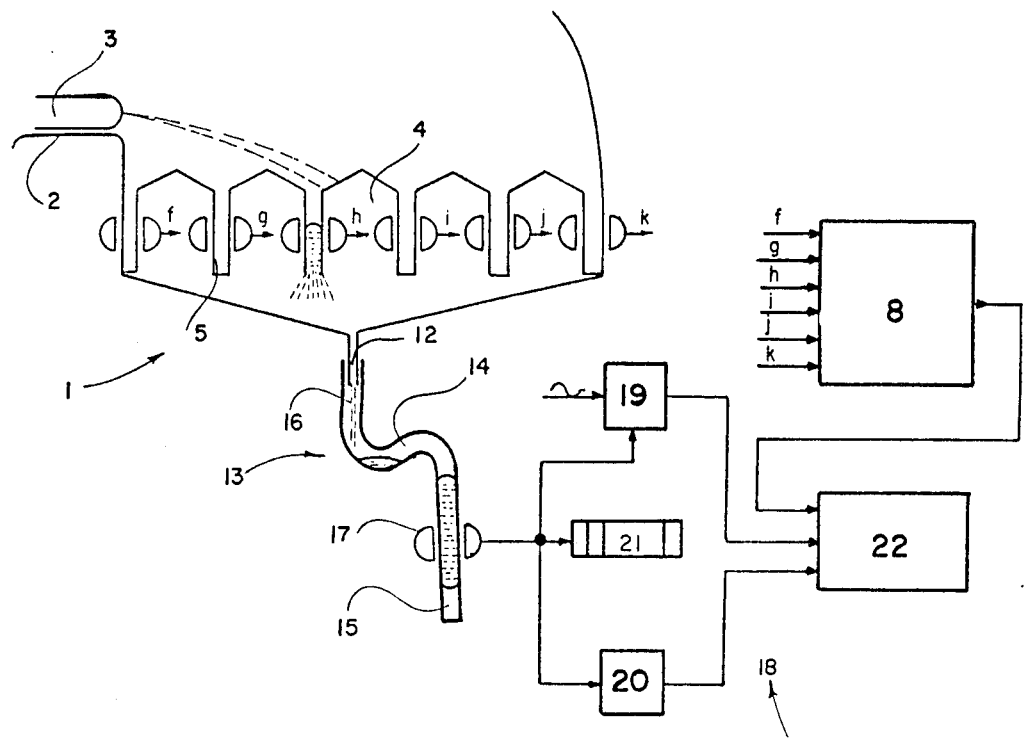
FIG. 1 is a view showing schematically a device for diagnosing and monitoring urological diseases in accordance with the present invention.
Figure 2:
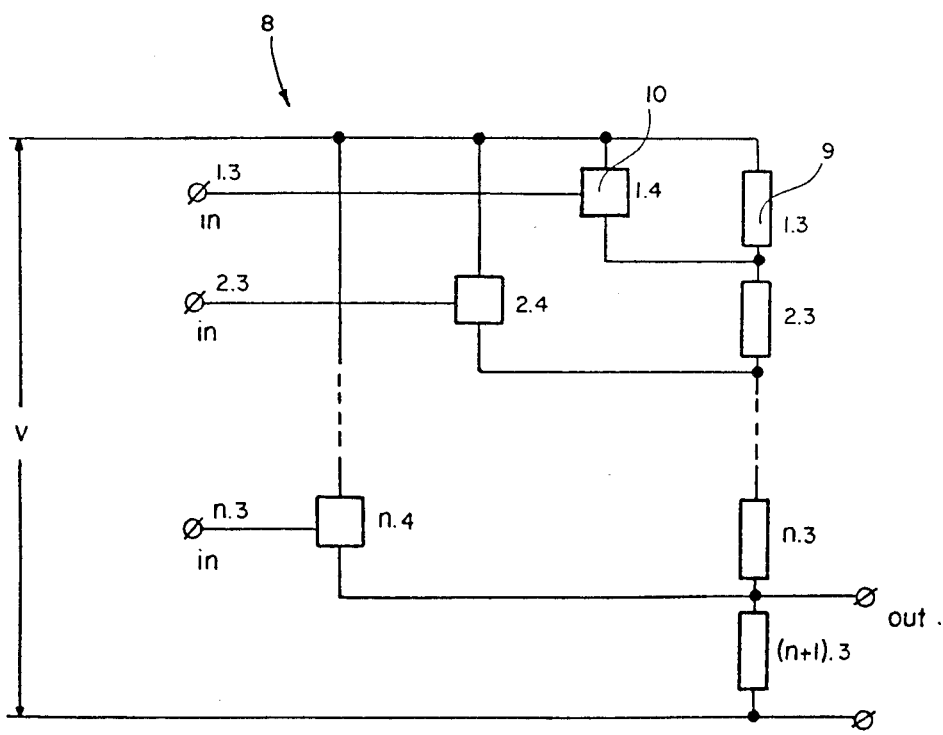
FIG. 2 is a view showing an element of one determining means, formed as a stepped potentiometer.

A device for diagnosing and monitoring urological diseases in accordance with the present invention includes several units, one of which is a unit for determining variations of an exit speed of a urine stream during urination of a patient. This unit is identified as a whole with a reference numeral 1. The unit 1 includes a support 2 for supporting of patient's urinating organ 3 in a horizontal position and at a predetermined height above a urine collector 4. The support 2 can be formed as a supporting plate, a pipe etc. The urine collectors 4 are located at the same height along an axis of the urinating organ 3 and spaced from the latter or from the front edge of the support 2 by differing distances. Each urine collector 4 has a draining pipe 5 through which urine flows into a common urine collector 6. Each pipe 5 is provided with a sensor 7 which generates a signal about flowing of urine through the respective pipe. Outlets of all sensors 7 are connected with inlets of a potentiometer unit 8 shown in FIG. 2.

The potentiometer unit 8 is a stepped potentiometer which is used for dividing of voltage applied thereto from a direct current voltage. The potentiometer has a plurality of resistors 9 with a plurality of normally open keys 10. The potentiometer has $n+1$ resistors $1.3-(n+1).3$ connected in series and n normally open keys $1.4-n.4$. When a signal is supplied from the unit 1 to i key of the potentiometer ($i = 1,2,\ldots, n$) i key turns to the closed position and shunts the resistors from 1.3 to i.3 and supplies voltage to the resistors from $(i+1).3$ to $(n+1).3$. The urine stream exiting from the urinating organ moves over a parabola, and depending upon its exit speed reaches the respective urine collector. The more is the exit speed of the urine stream, the more remote from the support 2 urine collector will be reaches by the urine stream, and the greater number of the resistors of the stepped potentiometer is shunted. With the increase of the number of shunted resistors $1.3-i.3$, the voltage drop at the resistor $(n+1).3$ increases, and therefore the outlet voltage of the unit 8 also increases. The sensors 7 can be used as the normally open keys $1.4-n.4$ in which with the aid of urine as a current conductive liquid it is possible to shunt the sections of the potentiometer. As a sensor, two electrodes can be used inserted into each pipe 5. When the urine stream reaches two or more urine collectors the outlet signal of the unit 8 does not change, since the unit always produces a signal corresponding to the farther distance from the support 2 or the urinating organ 3 or the maximum value of stream pressure corresponding to the maximum value of the exit speed of the urine stream.

It is to be understood that the potentiometer unit cam be separately connected with a recording or indicating device, such as a writer etc and therefore the variations of the exit speed of the urine stream will be continuously recorded. Abscissa of the writing satisfies the condition $$Y_i > Y_j \text{ if } l_i > l_j$$

wherein
$Y_i, Y_j$ are values of ordinates of writing of exit speed of urine stream exiting the urinating organ; and
$l_i, l_j$ are accordingly distances of i and j urine collectors from the end of the urinating organ or the support.

The variations in the exit speed of the urine stream is one of most important symptoms of urological diseases. When the exit speed is uniform over a period of time, this is a certain indication of a healthy urological system. Irregularities and sharp changes in the exit speed over time indicate abnormal condition of the urological system. The above described units can be used for monitoring the exit speed and correspondingly diagnosing and monitoring the urological diseases based on this characteristic. On the other hand, these units can also be connected with further units to provide a combined characteristic of the urination process, as will be described hereinbelow.

The common urine collector 6 of the unit 1 has an outlet pipe 12 introduced into an inlet of a dosing unit 13. The dosing unit 13 is formed as a capillary pipe having an inner diameter d and including a short section 14 and a long section 15. It also has an inlet formed by a vertical pipe 16. The upper end of the pipe 16 is higher than the height of the bend between the sections 14 and 15. The height h of the short section of the siphon 13 is greater than the diamter d. The siphon has an S-shaped part formed partially by the sections 14 and 15. This S-shaped part forms a dosing container, and the volume of urine accummulated therein must satisfy the condition $V > 1/6\pi d^3$. In other words the volume V of each urine dose must be greater than the volume of a sphere with a diameter equal to the diameter of the interior of the pipe. This provides for stability of formation of the urine doses and their separation by gas intervals(air) in the capillary pipe of the siphon.

The long section 15 is provided with a sensor 17 for sensing of the formed urine doses. When each urine dose passes through the section 15, one impulse is generated. It is possible to use photoelectric sensors for transparent liquids, so that the dose of liquid in the capillary pipe is used as a cylindrical lens for focusing of a beam of parallel rays onto the photosensor. Since the urine is current-conductive liquid, electric circuit from a current source can be closed through the urine dose and therefore electrical sensors can be used.

A next unit is identified with reference numeral 18 and includes a normally open time relay 19, a convertor "number-analog" or counter of impulse numbers-counter of average speed of impulses 20, a counter of impulses with a digital indication 21, and a registering (recording) element 22 such as a graph. The outlet of the sensor 17 is connected in parallel with the inlets of the counter 21, the convertor 20 and the starting inlet of the time relay 19. Through the latter, the circuit of the element 22 is closed. More particularly the circuit of a tape-transporting mechanism of the graph 22 is closed through the time relay 19. The outlet of the convertor is connected with the inlet of the recording element 22.

Figure 3:
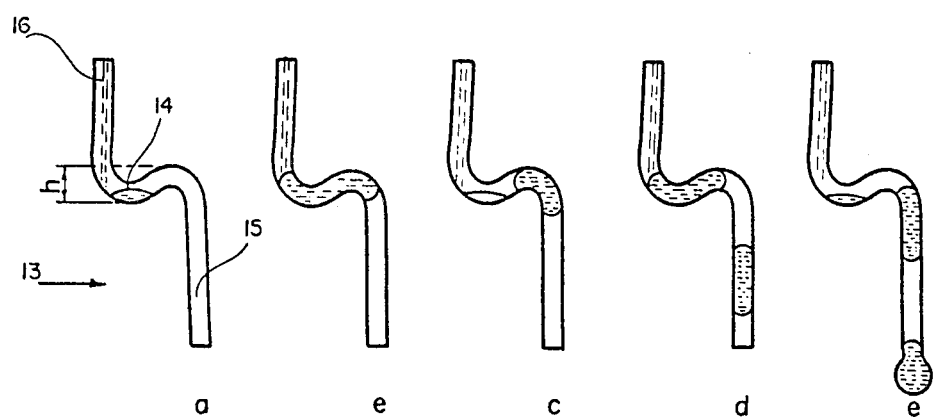
FIG. 3 is a view showing an element of anither determining means, formed as a siphon.

FIG. 3 shows the process of passing the urine through the dosing unit 13. The initial stage is shown in FIG. 3a. When the volume of the accumulated urine exceeds the volume of the dosing container and curved end portions of the urine enter the sections 16 and 15 of the capillary pipe, the condition is formed when the accumulated dose of urine lowers as a plug under the action of its weight along the section 15 and aspirates air from the surrounding through the pipe 16. This process takes place until a next dose closes the cross section of the section 14 in FIG. 3d. Under the action of the preceding dose of urine moving in the section 15, next doses of urine are aspirated into the section 15, as shown in FIG. 3e. This process is continuously repeated.

As a result of each passage of the urine dose through the section 15, the sensor 17 generates an impulse. When a first impulse is supplied into the closing inlet of the time relay 19, the latter closes the circuit of a drive of the tape-transporting mechanism of the recording element 22 with a current source for a time. Each subsequent impulse from its supply into the starting inlet of the time relay extends this condition for the time. Thus, starting from the moment of passage of the first urine dose through the sensor 17, the tape-transporting mechanism of the graph starts to work and registers the frequencies of passage of the urine doses as a function of time. After a time after supply of the last urine dose into the sensor 17 the current circuit of the tape-transporting mechanism is interrupted. Thus the recording element 22 is actuated automatically from the moment of penetration of the first urine dose into the sensor 17 and automatically disconnected after the time after the supply of the last urine dose. The counter 21 shows the total number of the urine doses formed during the certain period of time. The graph 22 shows the variations of quantity of urine over a period of time.

The units 13 and 18 can be used separately so as to only monitor the variations of the quantity of urine exiting as a function of time. This characteristic is also an important symptom of condition of the urological system.

Figure 4:
FIG. 4 is a view schematically showing the arrangement of units of the inventive device.

In accordance with the present invention is, however possible, to determine two characteristics of the urination process, namely the variations of the exit speed and the varistions of the quantity of urine as a function of time. For this purpose the unit 1 is connected, as shown, with the unit 13 and therefore with the unit 18. The recording element 22 is formed as a two channel element and connected both with the member 8 of the unit 1 and the members 20 and 19 of the unit 18. As can be seen from FIG. 4, the graph 22 writes two characteristic lines corresponding to the respective characteristics. Moreover, the unit 1 into which a patient urinates can be located remotely from the element 22, for example in a bathroom. The element 22 which shows the required characteristics can be located, in turn, directly in a physicians room. The element 22 can be formed as a graph, a digital display etc.

The device in accordance with the present invention can be used for diagnosing and monitoring of urological diseases, such as prostate, phimosis, bed-wetting and others. It can also be used for diagnosing and monitoring of venereal diseases which affect the process of urination. It is to be understood that tests must be conducted to determine the relationship between respective diseases and their stages with variations in the exit speed and quantity of urine per time unit.

The invention is not limited to the details shown since various modifications are possible without departing from the spirit of the invention.

What is desired to be protected in set forth in the appended claims.

I claim:

1. A device for diagnosing and monitoring urological diseases, comprising means for determining variations of an exit speed of a urine stream during urination of a patient over a period of time as a function of time, said determining means including a plurality of first sensing elements arranged successively one after the other and therefore at different distances from a point of urine stream exit and having inputs formed so that a urine stream flowing out of a patient directly reaches a respective one-of-said sensing elements without passing through intermediate elements, so that when the urine stream reaches a respective one of said first sensing elements a signal is produced which corresponds to its distance from the urine exit point of a patient and is therefore an indication of the linear exit speed of the urine stream; means for producing said signal; and selecting means cooperating with said determining means so that in the event when the urine stream reaches more than one of said sensing elements the signal is produced by only such sensing element which is located further from the urine exit point.

2. A device as defined in claim 1, and further comprising second determining means arranged to determine variations in a quantity of urine flowing out during urination of a patient, over period of time, synchronously with determination of variations of the exit speed.

3. A device as defined in claim 2, wherein said second determining means includes a separating element which subdivides the urine stream into a plurality of successively flowing urine doses, and a second sensing element cooperating with said separating element and arranged to detect said urine doses during their successive flow.

4. A device as defined in claim 3, wherein said separating element includes an upper substantially vertical receiving pipe, and a siphon having an upper substantially S-shaped section connected with said receiving pipe and a lower substantially vertical pipe connected with said S-shaped section.

5. A device as defined in claim 4, wherein said siphon has an inner diameter d, said S-shaped section of said siphon having a height which is greater than $1/6\pi d^3$, wherein d is said inner diameter.

6. A device as defined in claim 2, wherein said first mentioned determining means is arranged to produce first signals corresponding to the variations of the linear exit speed, whereas said second determining means is arranged to produce second signals corresponding to the variations of the urine quantity; and further comprising means for receiving said first and second signals and simultaneously displaying the latter.

7. A device as defined in claim 6, wherein said receiving and displaying means includes a graph with a tape of which simultaneously characteristics lines corresponding to said first and second signals are recorded.

8. A device as defined in claim 1, wherein said selecting means includes a stepped potentiometer having a plurality of resistors which are connected in series with said first sensing elements of said first determining means.

9. A device as defined in claim 1; and further comprising means for receiving said signals and displaying them.

10. A device as defined in claim 1, wherein said determining means includes a urine receiving element to be used by a patient, and a characteristic recording element to be monitored by a physician and the like, said urine receiving element and said characteristic recording element being formed as separate units so that they can be located remotely from one another.

* * * * *